March 3, 1959 C. C. SCOTT Plant Pat. 1,815
AVOCADO TREE
Filed July 16, 1956
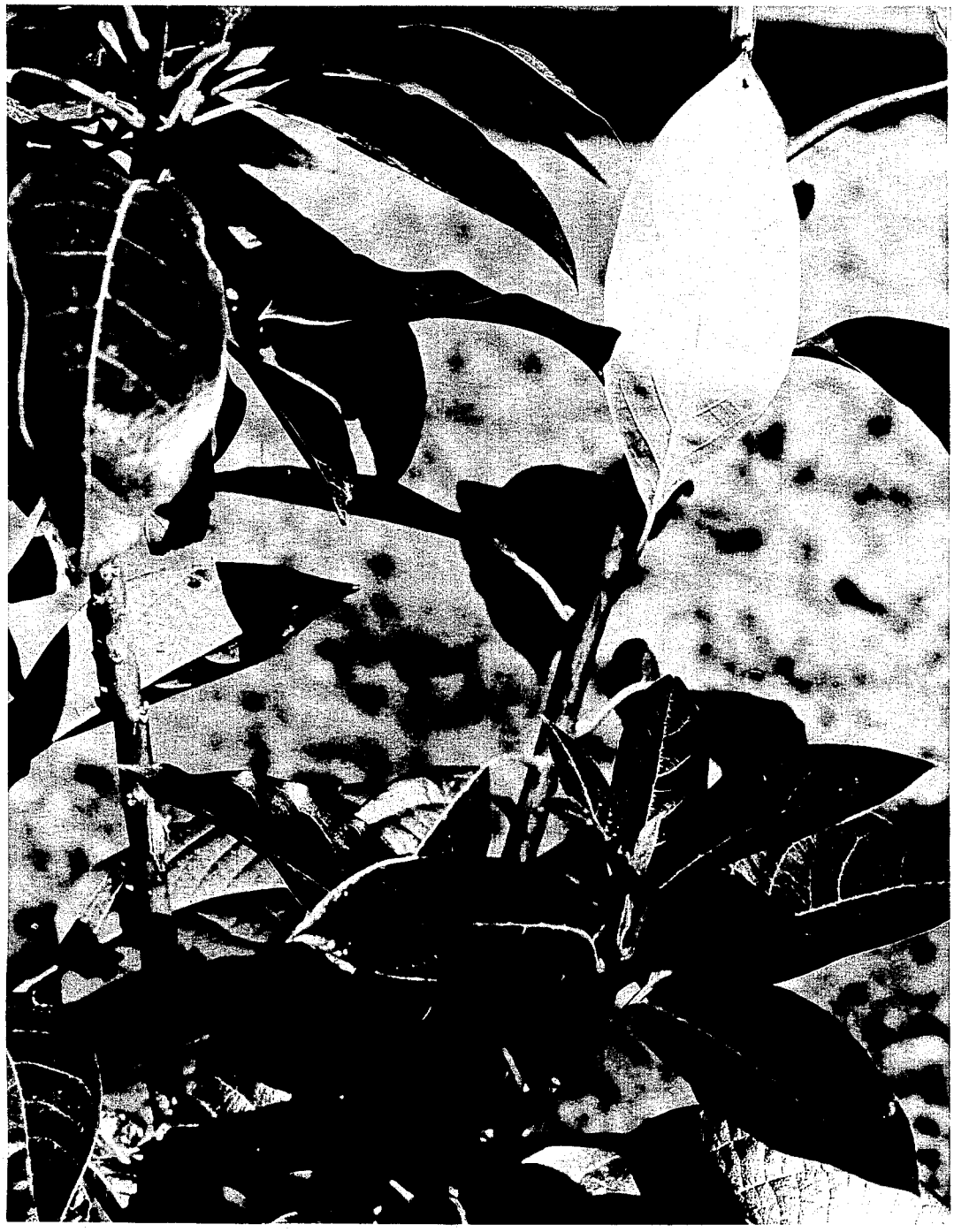
INVENTOR
CHARLES C. SCOTT
BY Richard L. Jamowitz
ATTORNEY United States Patent Office Plant Pat. 1,815
Patented Mar. 3, 1959

1,815

AVOCADO TREE

Charles C. Scott, Santa Ana, Calif.

Application July 16, 1956, Serial No. 598,222

1 Claim. (Cl. 47—62)

This invention relates to a new and distinct variety of avocado tree.

The principal disease of the avocado industry in California is *Phytophthora cinnamomi* (avocado root rot fungus). This disease, usually called cinnamon fungus, has already spread throughout southern California, and unofficial estimates indicated that 3,000–4,000 acres had been affected in southern California as of the summer of 1955. In view of this fact, it has been an urgent necessity for the avocado industry to find a rootstock which is resistant to the fungus, or which will grow so vigorously in infected soil that the avocado tree will remain healthy regardless of infection.

The problem of finding such a rootstock has been compounded by the fact that rootstocks presently in use are seedling avocados, and due to the variability of seedlings and the variations in compatibility of scions with rootstocks, the resultant orchard trees are not uniform in growth or production. It has therefore been necessary to develop a satisfactory method of reproducing identical rootstocks, enabling the grower to develop an orchard of identical trees, such trees being capable of remaining healthy in soil infected with cinnamon fungus. In this connection it is emphasized that cuttings of most avocado varieties are difficult to root by conventional methods, although many varieties may be rooted by highly expensive and time-consuming greenhouse methods.

In 1952 applicant discovered that one old tree, located in Santa Ana, California, was in excellent condition, even though most of the trees adjacent to it had died or had been replaced because of avocado root rot (cinnamon fungus). This tree was approximately 35 years old at the time, and the anise odor of the leaves suggests that the rootstock is a Mexican seedling (unpatented). The fruiting top of the tree is of the Fuerte variety (unpatented). Several suckers were growing out of this tree from the rootstock, i. e. from a point below the bud union of the rootstock with the Fuerte top, and these suckers were employed to asexually reproduce the rootstock. As will be described subsequently, the resulting tree not only flourishes in orchard soil infected with cinnamon fungus, but has exhibited surprising resistance to lime-induced chlorosis and other undesirable conditions. Furthermore, and very importantly, the avocado tree of the invention may be rooted almost 100% by conventional methods, which means that the tree may be reproduced in kind and that the seedling method of rootstock propagation need no longer be employed.

The avocado tree of the invention has been reproduced by applicant near Santa Ana, California, by rooting cuttings of the above-mentioned suckers (and descendants thereof) by conventional methods. The tree has also been reproduced, by permission of applicant, at the University of California at Los Angeles. Such reproduction at the University of California at Los Angeles was by conventional rooting techniques, and also by a graftingetiolation method described in the California Avocado Society Yearbook for the year 1951, pages 136–138.

One of the trees thus propagated, and which is presently growing near Santa Ana, California, in infected soil near the old parent tree above referred to, is illustrated in the appended color photograph. The illustrated tree was approximately 10 months old when photographed, and was reproduced by rooting by conventional methods. The leaves shown are those of the rootstock, no fruiting top having been grafted thereon. In the photograph, the budding wood is shown at the left, and younger wood at the right. One leaf (upper right) has been turned up to show the color and veining on the underside thereof. A number of leaves have been removed in order to better illustrate the markings and buds on both the budding and younger wood. No fruit has been illustrated since, as far as is presently known, the tree is sterile in that it produces no fruit or seeds although it does produce flowers.

As shown in the color photograph, the leaves are simple and elongated, the edges being only slightly undulant. The leaves appear to emanate from nodes about 120 degrees from each other. The relatively young stem growth, as shown at the right in the photograph, is characterized by light-brown markings. The older, budding branches, as shown at the left in the photograph, are covered by a bark which does not have the light-brown markings. In accordance with the conventional rooting techniques above indicated, at least two buds of the type shown at the left in the photograph must be retained on the cutting that is rooted.

The color of the leaves varies greatly in accordance with the age of the plant, soil conditions, fertilizer, and time of year. Mature leaves compared with the plates in Ridgway, Color Standards, were colored Spinach Green (Plate V), Forest Green (Plate XVII), or Grass Green (Plate VI). The face of the leaf is shiny, and is characterized by distinct veining which is generally an Oil Yellow (Plate V). The underside or back of a mature leaf, as shown at the upper right in the photograph, is generally dull and of a green such as Bice Green (Plate XVII), being prominently veined. New immature leaves are lighter in color, and are frequently of a grayish-red color as shown in the lower right portion of the photograph.

The leaves may grow to relatively large size, mature leaves having been measured at 12 inches in length and 5½ inches in width. A characteristic of the tree is the particularly strong anise odor of the leaves, especially after they are crushed in the hand.

As previously indicated, a primary characteristic of the tree is its ability to flourish in soil infected with cinnamon fungus, the illustrated plant being one growing in infected soil where mature avocado trees had previously died of the fungus. Although it has sometimes been possible to infect the present rootstock with cinnamon fungus during greenhouse tests, cuttings planted in infected orchards are still growing vigorously over two years after they were set out. The tree is characterized by extremely rapid and vigorous growth, and the possibility exists that the tree flourishes in infected soil since the roots are produced faster than they can be destroyed by the fungus. Regardless of the theory, the fact remains that a substantial number of the trees are flourishing, and in perfect condition, in soil infected with cinnamon fungus.

In addition to its characteristics of extremely vigorous growth and large leaves, a further characteristic is that the tree is apparently sterile. Cytogenetic observations on the flowers produced by the present tree indicate that it is a variable multiploid which may be sterile. No fruit has been produced on any of the trees propagated to date.

Nutritional studies with the present tree in a glasshouse have indicated that it is extremely resistant to lime-induced chlorosis. It appears to be more resistant than most Mexican seedlings, which generally exhibit greater resistance to lime-induced chlorosis than do Guatemalan seedlings.

In other studies it has been observed that cuttings of the present tree were not injured by sodium bicarbonate or sodium chloride after applications equal to those that caused severe injury to other avocado materials. Application of 25 grams of sodium chloride to the present trees in five-gallon cans caused no injury whatsoever. Sodium had not translocated to the leaves of the plants, and only 0.55% chlorine was present in the leaves 14 days after application. This is ¼–⅓ as much leaf chlorine as has been observed for other avocado materials in pots.

As previously indicated, a highly important distinguishing characteristic of the present tree is that it is easily propagated by means of cuttings, no seedlings being needed. The tree appears to be compatible, at least with the more common fruiting tops such as the Fuerte (unpatented) and Haas (expired Plant Patent No. 139), graftings with both of such varieties having been performed successfully. It appears to be a characteristic of the tree, however, that the grafting with the fruiting top should not be made without leaving at least two leaves on the present rootstock. A number of graftings made without leaving leaves on the rootstock have resulted in death of the plants.

I claim:

A new and distinct variety of avocado tree substantially as disclosed, characterized by its rapid and vigorous growth, its ability to flourish in soil infected with *Phytophthora cinnamomi*, its resistance to lime-induced chlorosis, its high tolerance to sodium bicarbonate and sodium chloride, its distinct ease of rooting, its sterility, and the strong anise odor of its leaves.

No references cited.